(12) United States Patent
Melvin et al.

(10) Patent No.: US 9,492,270 B2
(45) Date of Patent: Nov. 15, 2016

(54) MEDICAL DEVICE AND TENSION MEMBER FOR USE IN A SUBJECT

(76) Inventors: Alan Joel Melvin, Cincinnati, OH (US); Dennis R. Trumble, Pittsburgh, PA (US)

( * ) Notice: Subject to any disclaimer, the term of this patent is extended or adjusted under 35 U.S.C. 154(b) by 1343 days.

(21) Appl. No.: 12/678,008

(22) PCT Filed: Sep. 12, 2008

(86) PCT No.: PCT/US2008/076188
§ 371 (c)(1),
(2), (4) Date: Aug. 9, 2010

(87) PCT Pub. No.: WO2009/036286
PCT Pub. Date: Mar. 19, 2009

(65) Prior Publication Data
US 2010/0298935 A1    Nov. 25, 2010

Related U.S. Application Data

(60) Provisional application No. 60/993,430, filed on Sep. 12, 2007.

(51) Int. Cl.
*A61F 2/08* (2006.01)

(52) U.S. Cl.
CPC ........ *A61F 2/0811* (2013.01); *A61F 2002/087* (2013.01); *A61F 2002/0829* (2013.01);
(Continued)

(58) Field of Classification Search
CPC ............ A61F 2/0811; A61F 2002/0829; A61F 2002/0852; A61F 2002/087
(Continued)

(56) References Cited

U.S. PATENT DOCUMENTS 3,753,551 A  *  8/1973  Tidwell .......................... 114/218
4,793,335 A  * 12/1988  Frey et al. .................. 623/13.14
(Continued)

FOREIGN PATENT DOCUMENTS

AU       769195 B2    1/2004
CA      2364351 A1    7/2000
(Continued)

OTHER PUBLICATIONS

International Searching Authority, Search Report and Written Opinion received in PCT/US08/76188 dated Nov. 10, 2008, 11 pp.

*Primary Examiner* — Brian Pellegrino
(74) *Attorney, Agent, or Firm* — Wood Herron & Evans LLP

(57) ABSTRACT

A medical device and tension member for use in a subject enables fixation of tension members and transmission of force from tissues to energy converters or to natural or prosthetic bones or other prostheses. The medical device includes an anchor block having a knob extending from its surface, such knob configured to engage a looped tension member. The tension member includes a looped portion configured to engage the knob, an intermediate portion, and a tissue engaging portion configured to engage tissue in a subject. The looped portion is connected to the tissue engaging portion via the intermediate portion. A system is provided for use in a subject and includes at least one looped tension member, an operational device, and at least one medical device configured to couple the looped tension member and the operational device.

18 Claims, 12 Drawing Sheets

(52) U.S. Cl.
CPC *A61F 2002/0852* (2013.01); *A61F 2002/0888* (2013.01)

(58) Field of Classification Search
USPC .............. 623/13.13, 13.14, 13.19, 908, 13.2; 606/281, 74, 280, 130, 151; 114/218
See application file for complete search history.

(56) References Cited

U.S. PATENT DOCUMENTS

| | | | |
|---|---|---|---|
| 4,932,972 A | | 6/1990 | Dunn et al. |
| 4,942,875 A | * | 7/1990 | Hlavacek et al. ......... 623/13.19 |
| 4,976,719 A | * | 12/1990 | Siepser ........................ 606/151 |
| 5,109,843 A | | 5/1992 | Melvin et al. |
| 5,151,104 A | * | 9/1992 | Kenna .................. A61F 2/0811 623/13.14 |
| 5,197,983 A | * | 3/1993 | Berman et al. ............. 623/13.2 |
| 5,556,428 A | * | 9/1996 | Shah ........................ 623/13.13 |
| 5,718,248 A | | 2/1998 | Trumble et al. |
| 5,725,582 A | * | 3/1998 | Bevan ............... A61B 17/7022 623/13.12 |
| 5,800,543 A | * | 9/1998 | McLeod et al. ........... 623/13.19 |
| 5,888,186 A | | 3/1999 | Trumble et al. |
| 5,957,977 A | | 9/1999 | Melvin |
| 6,032,076 A | | 2/2000 | Melvin et al. |
| 6,190,408 B1 | | 2/2001 | Melvin |
| 6,214,047 B1 | | 4/2001 | Melvin |
| 6,221,103 B1 | | 4/2001 | Melvin |
| 6,409,760 B1 | | 6/2002 | Melvin |
| 6,520,904 B1 | | 2/2003 | Melvin |
| 6,529,765 B1 | * | 3/2003 | Franck et al. ................ 606/130 |
| 6,558,389 B2 | * | 5/2003 | Clark et al. ..................... 606/60 |
| 6,582,375 B2 | | 6/2003 | Melvin et al. |
| 6,592,619 B2 | | 7/2003 | Melvin |
| 6,626,944 B1 | * | 9/2003 | Taylor ............... A61B 17/7062 606/263 |
| 6,733,510 B1 | | 5/2004 | Melvin |
| 6,988,982 B2 | | 1/2006 | Melvin et al. |
| 7,081,084 B2 | | 7/2006 | Melvin |
| 7,361,191 B2 | | 4/2008 | Melvin |
| 7,367,978 B2 | * | 5/2008 | Drewry .............. A61B 17/7022 606/74 |
| 7,658,705 B2 | | 2/2010 | Melvin et al. |
| 7,662,085 B2 | | 2/2010 | Melvin |
| 7,715,918 B2 | | 5/2010 | Melvin |
| 7,753,837 B2 | | 7/2010 | Melvin |
| 2002/0022880 A1 | | 2/2002 | Melvin |
| 2002/0111533 A1 | | 8/2002 | Melvin |
| 2003/0023132 A1 | | 1/2003 | Melvin et al. |
| 2004/0015040 A1 | | 1/2004 | Melvin |
| 2004/0015041 A1 | | 1/2004 | Melvin |
| 2004/0059180 A1 | | 3/2004 | Melvin |
| 2004/0064014 A1 | | 4/2004 | Melvin et al. |
| 2004/0078089 A1 | * | 4/2004 | Ellis et al. .................... 623/13.2 |
| 2004/0097942 A1 | * | 5/2004 | Allen et al. ...................... 606/72 |
| 2005/0033301 A1 | * | 2/2005 | Lombardo ......... A61B 17/1714 524/556 |
| 2005/0049702 A1 | | 3/2005 | Melvin |
| 2005/0250976 A1 | | 11/2005 | Melvin et al. |
| 2006/0178551 A1 | | 8/2006 | Melvin |
| 2006/0187550 A1 | | 8/2006 | Melvin |
| 2007/0239275 A1 | * | 10/2007 | Willobee ................. A61F 2/08 623/13.17 |
| 2008/0269894 A1 | | 10/2008 | Melvin |
| 2009/0216252 A1 | | 8/2009 | Melvin et al. |

FOREIGN PATENT DOCUMENTS

| | | |
|---|---|---|
| DE | 60011407 T2 | 6/2005 |
| EP | 1164941 A1 | 1/2002 |
| EP | 1631348 A2 | 3/2006 |
| EP | 1720461 A2 | 11/2006 |
| WO | 2004006752 A2 | 1/2004 |
| WO | 2004008940 A2 | 1/2004 |
| WO | 2004008941 A2 | 1/2004 |
| WO | 2004016159 A2 | 2/2004 |
| WO | 2004026121 A2 | 4/2004 |
| WO | 2004110257 A2 | 12/2004 |
| WO | 2004110307 A2 | 12/2004 |
| WO | 2004110334 A1 | 12/2004 |
| WO | 2004110553 A1 | 12/2004 |
| WO | 2005079388 A2 | 9/2005 |
| WO | 2006074413 A2 | 7/2006 |
| WO | 2009036286 A1 | 3/2009 |
| WO | 2009076209 A1 | 6/2009 |

* cited by examiner

MEDICAL DEVICE AND TENSION MEMBER FOR USE IN A SUBJECT

CROSS REFERENCE TO RELATED APPLICATION

This application claims the benefit of U.S. Provisional Application Ser. No. 60/993,430, filed Sep. 12, 2007, entitled "Tension Member for Use With A Subject and Method, System and Attachment Regarding Tension Member", the disclosure of which is hereby incorporated by reference herein in its entirety.

FIELD OF THE INVENTION

The present invention relates generally to fixation of tension members such as artificial tendons and to transmitting force from tissues such as skeletal muscles to energy converters or to natural or prosthetic bones or other prostheses.

BACKGROUND

Fixation of prosthetic flexible tension members to relatively rigid structures has been a serious problem. A notable example is the use of artificial ligaments, such as the Leeds-Keio anterior cruciate ligament replacement in the knee. In that example, published experience with the usual means of bone fixation—drilling a hole in the tibia, inserting the tendon, and securing with a suture or pin—has included several instances of fragmentation of the polyester fibers of the prosthesis within a few months to a few years. A compression plate fixation has also been used whereby tension members are cut and the end grasped between two plates, generally textured and held together by compression screws to grasp the tension member. While this allows greater control of local stress concentration than does a simple bone-hole, in theory, it delivers extremely high shear stresses to the tension member locally, which may cause fatigue failure and breakage over the immense number of stress cycles expected to be required.

Natural tendon ends, which are living tissue, have been connected to 'towel bar' fixtures on artificial bones, over which they are looped and sewn. Because of the shape of tendons, generally flattened in the plane of attachment, the axis of curvature is generally parallel to the surface to which they are to be attached. To avoid intolerable protrusion dimensions into surrounding tissue structures, the radius of curvature is very small. Since the compressive stress on a tension member surface, when that tension member is looped about any rod or pulley, is directly proportional to the tension applied and inversely proportional to both the radius of curvature and the projection of contact surface perpendicular to the transmitted tension, compressive forces intolerable by the tension member may be generated.

There is thus a need in the art for an artificial force-transmitting tension member, such as an artificial tendon, that can be formed in a circular or other stable cross-sectional configuration so as to allow a medical device to be relatively narrow, flat, and oriented in the plane of the surface to which the tension member is to be attached. In this way, the radius of curvature may be made substantially larger than achievable with the 'towel bar' concept, and yet with only minimal protrusion into surrounding tissue structures. And, the presenting surface of the knob and of any secondary caps may be readily shaped such that minimal protrusion would present a smooth surface to the overlying skin or other tissue.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

In one embodiment, a medical device is provided for engaging at least one tension member. The medical device includes an anchor block configured to be implanted in a subject and having at least one knob extending from its surface. The knob is configured to engage a looped tension member and can be shaped similarly to a simple pulley. A cap can be disposed on at least a portion of the knob so as to help prevent the tension member from coming off the knob and to minimize potential spaces for localization of tissue fluid. The knob can include an optional channel to receive the looped tension member, which is at least in part an arc, generally a circular or elliptical arc, generally in one plane, with a change in orientation over its course between 90 and 270 degrees.

In another embodiment, a tension member is provided which is configured for use in a subject. The tension member includes at least one looped portion, an intermediate portion, and a tissue engaging portion. The looped portion is connected to the tissue engaging portion by the intermediate portion. The looped portion, the intermediate portion, and the tissue engaging portion define a continuous unit. The tissue engaging portion is configured to engage a tissue in a subject.

In yet another embodiment, a system is provided for providing a function to a subject. The system includes at least one looped tension member, an operational device, and at least one medical device configured to couple the looped tension member and the operational device, with improved stress distribution in the tension member. The medical device has an anchor block configured to engage the operational device and a knob which extends from the anchor block. The looped tension member has a looped portion configured to engage the knob and a tissue engaging portion configured to engage a tissue in a subject. The operational device performs the function in the subject. The operational device can be a relatively rigid structure, natural or prosthetic.

In still another embodiment, a method for implanting a medical device in a subject is provided. The method includes the steps of positioning a medical device including an anchor block having at least one knob within a subject, then placing at least one looped portion of a looped tension member having a tissue engaging portion about the knob. A cap and/or rim of the knob aid in position maintenance of the looped tension member, with tension being delivered, generally equally, to two extending ends of the tension member.

BRIEF DESCRIPTION OF THE DRAWINGS

In the accompanying drawings, the preferred embodiment of the invention and preferred methods of practicing the invention are illustrated in which.

DETAILED DESCRIPTION OF THE INVENTION

Figure 1:
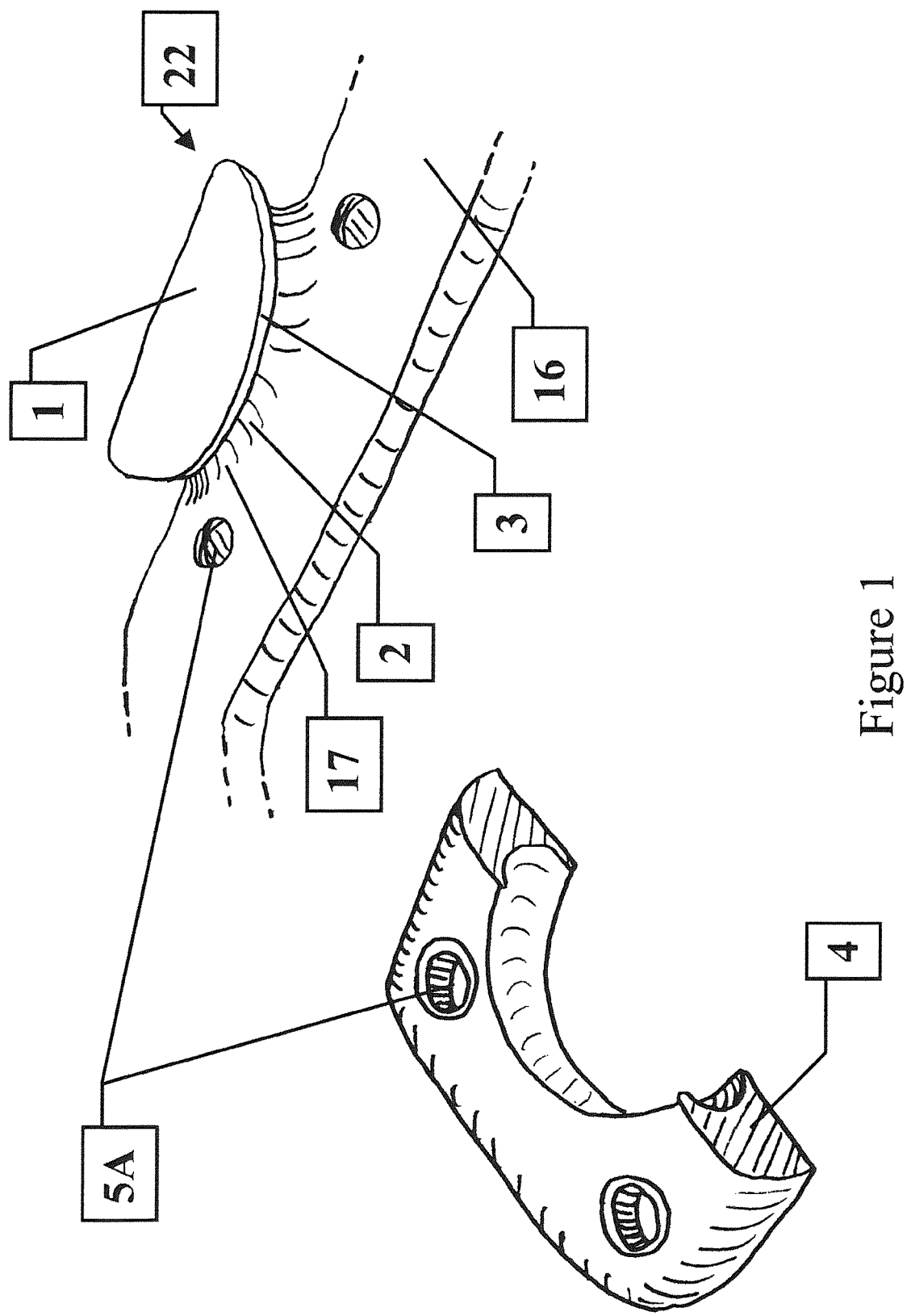
FIG. 1 is a perspective view of a medical device in accordance with an embodiment of the present invention.

One or more specific embodiments of the present invention will be described further below. In an effort to provide a concise description of these embodiments, all features of an actual implementation may not be described in the specification. It should be appreciated that in the development of any such actual implementation numerous implementation-specific decisions must be made to achieve the developers' specific goals, which may vary from one implementation to another. Moreover, it should be appreciated that such a development effort might be complex and time consuming, but would nevertheless be a routine undertaking for those of ordinary skill having the benefit of this disclosure.

When introducing elements of the present invention (e.g., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements.

Part Numbers
1. knob
2. channel for tension member
2A. example of channel 2 with arc having a convex curve surface
3. rim of knob
4. cap
5. example of means of securing of cap and/or knob (screw)
5A. example of means of securing of cap and/or knob (hole)
6. looped tension member
6A. conventional tension member
7. elastomeric sheath to cushion compressive force delivered to tension member surface.
8. bone plate
9. compression plate
11. loop portion
12. two 'arms' of a looped tension member
13. bundles or tows of fibers
14. surgical needles
15. a band incorporated in the loop to aid stability of position
16. actuator arm
17. anchor block
18. operational device- energy converter
19. intermediate portion
20. flare channel
21. tissue engaging portion
22. medical device Referring now specifically to FIGS. 1-3 and 9-11, the invention in one embodiment includes a medical device 22 having an anchor block 17 configured to be implanted in a subject. The medical device further includes at least one knob 1 extending from the anchor block 17. The knob 1 has at least one channel 2 (or groove) that helps maintain one or more looped tension members 6 whose stable position in channel(s) 2 may be aided by one or more bounding rims 3. The knob 1 is flattened such that the diameter of the knob 1 at the widest portion is greater than the height of knob 1. The knob is further specified and distinguished from rods or alternative means by its aspect ratio, in that potential height of the channel (the dimension spanning the possible position(s) of looped tension member(s) 6 in the direction perpendicular to the plane (or nonplanar surface) traced by the path of the loop of tension member 6) is less than one-half the length over which the looped tension member 6 is in contact with channel 2 during use. The channel 2 is at least in part an arc having a convex curved surface 2A, generally a circular or elliptical arc, generally in one plane, with a change in orientation over its course between 90 and 270 degrees. The plane of the channel can be oriented to include the usual range of force directions expected in the tension member.

There may be one or more structural components, such as cap 4, adding stability to the position of tension member 6 within channel 2. There may also be one or more means, such as screw 5, extending through a hole 5A, to secure the position of cap 4 and/or knob 1. Between the looped tension member 6 and channel 2, and/or between the looped tension member 6 and cap 4, there may be a compressible sheath 7 (FIG. 2) of a soft material such as an elastomeric polymer to further lessen potential stress concentration in looped tension member 6. The sheath 7 may be fixed to the looped tension member 6, fixed to the knob 1, or simply positioned between the two.

Figure 9B:
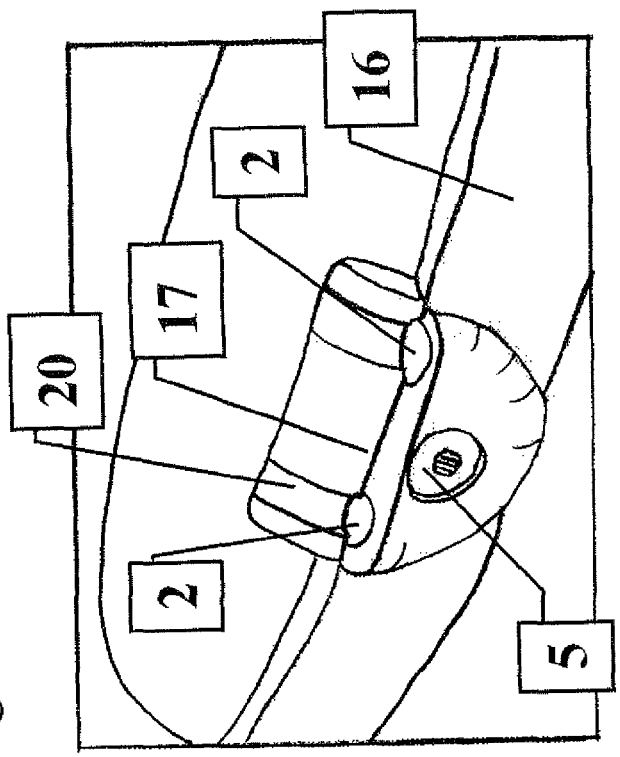
FIG. 9B is a perspective view of a medical device in accordance with yet another embodiment of the present invention on an actuator arm.
Figure 9A:
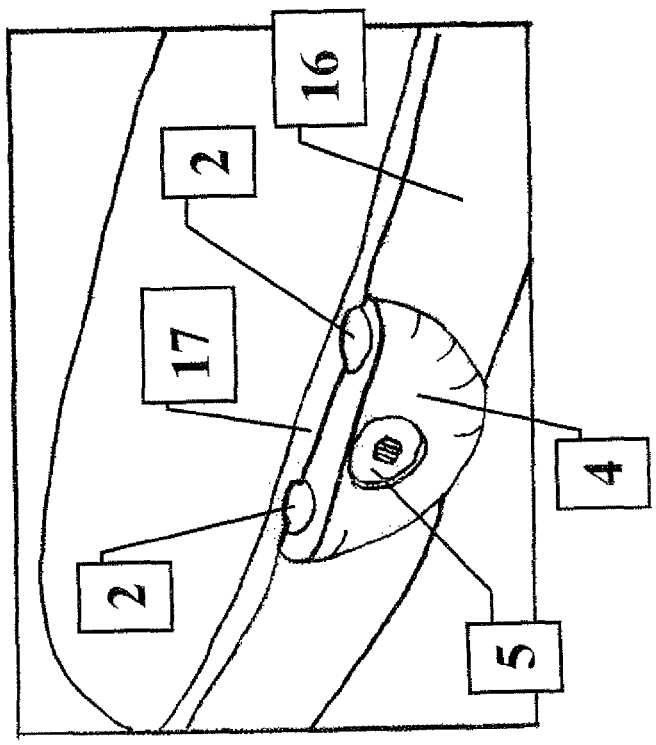
FIG. 9A is a perspective view of a medical device in accordance with another embodiment of the present invention on an actuator arm.
Figure 10:
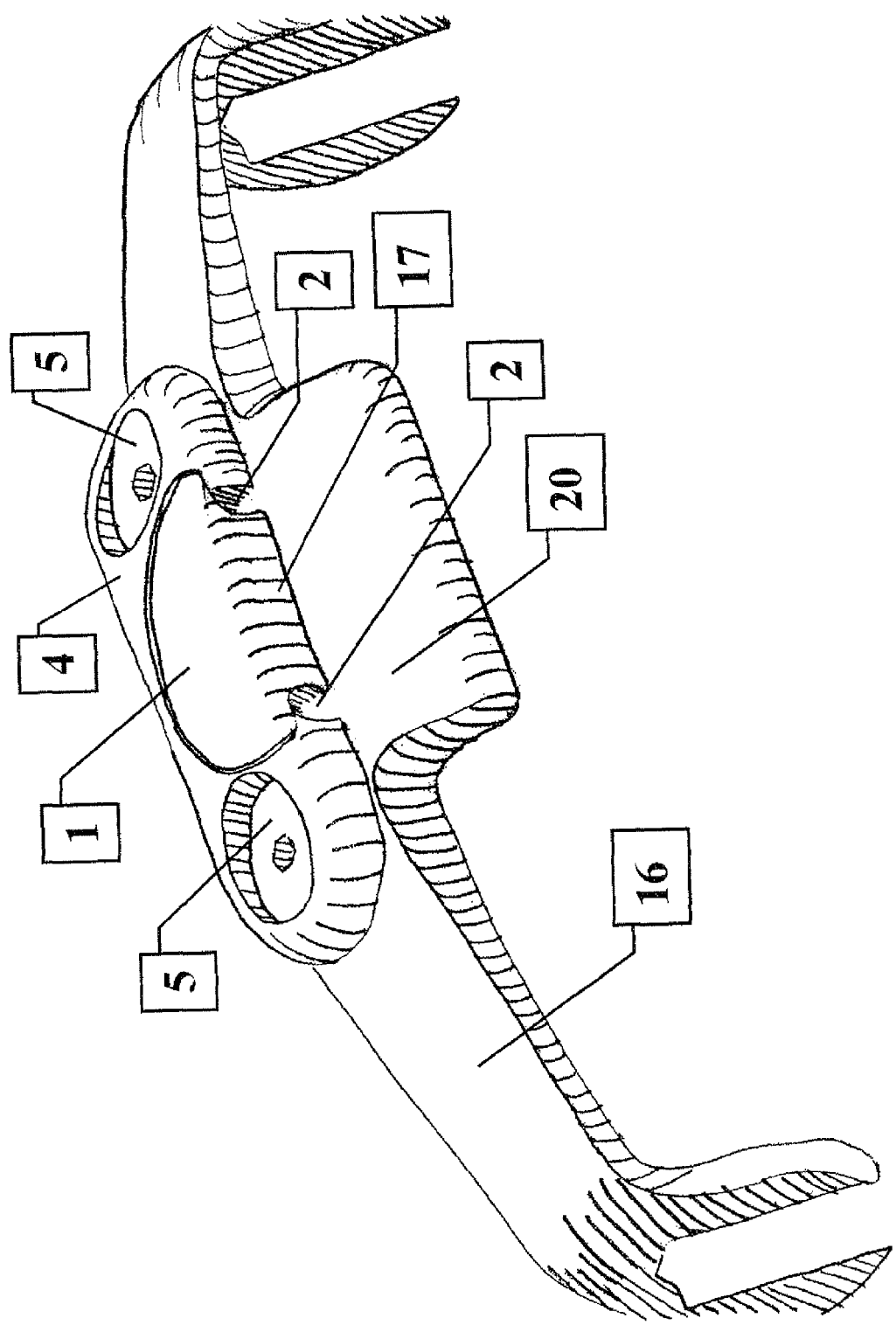
FIG. 10 is a perspective view of a medical device in accordance with yet another embodiment of the present invention on an actuator arm.
Figure 11:
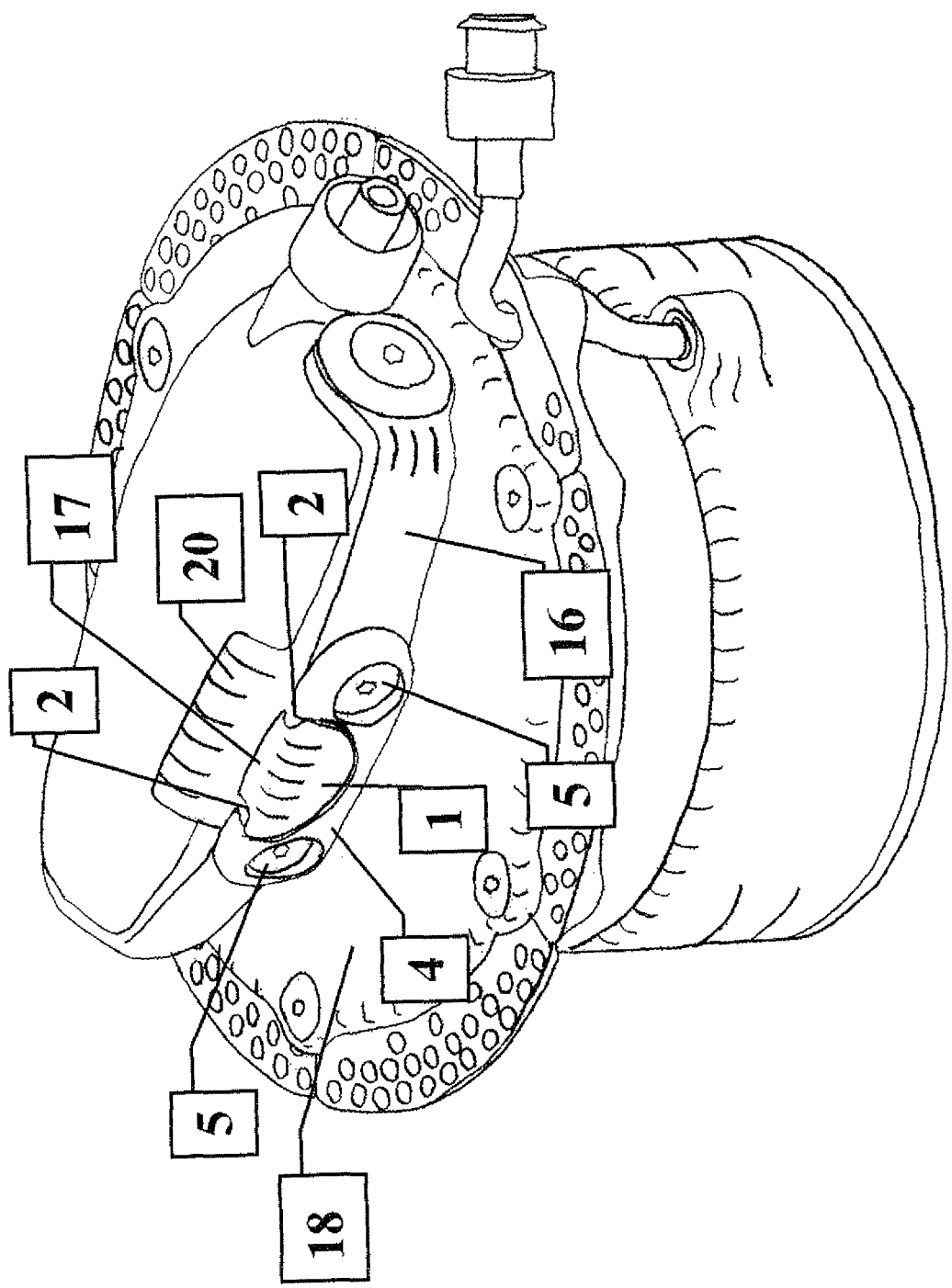
FIG. 11 is a perspective view of the medical device and actuator arm of FIG. 10 coupled to an energy converting device.

With further reference to FIGS. 1-3 and 9-11, the knob 1 protrudes from anchor block 17 which defines an actuator arm 16. The actuator arm 16, as best shown in FIG. 11, can be attached to an operational device, such as muscle energy converter (MEC) 18 which, in turn, is wired to a chest wall. Screws 5 secure the cap 4 to the actuator arm 16 to keep looped tension member 6 from disengaging knob 1.

The knob 1 can be made of anything that is a) biocompatible, and b) capable of withstanding the stresses delivered by the tension member. This includes, but is not limited to metals such as titanium or stainless steel (i.e., 316L stainless steel), metal alloys, ceramics, high molecular weights polymers, etc. The knob 1 may range from a few millimeters in diameter for small muscles like those found in the jaw, feet, and hands, to several centimeters in diameter for larger muscles like the latissimus dorsi. In one embodiment, the height of the knob 1 should be minimal and not exceed 5 mm In other embodiments, the height should not exceed 4 mm, 3 mm, or 2 mm.

Figure 4:
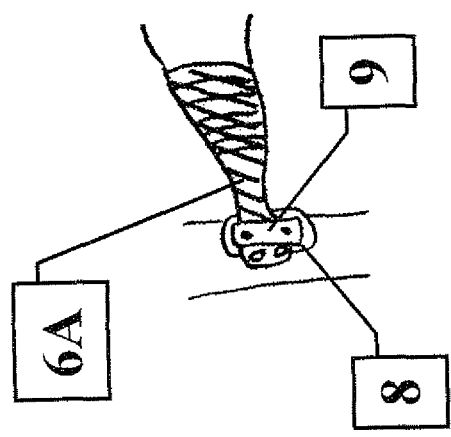
FIG. 4 illustrates conventional fixation of a tension member by a compression plate.

One aspect of the invention involves eliminating the stress concentration that is inherent in compressive type fittings. As illustrated in the bone plate screw compression of FIG. 4, the entire force applied to the conventional tension member 6A is countered by compression of the tension member 6A itself between a bone plate 8 and compression plate 9. Since the conventional tension member 6A may be of materials in which fatigue failure secondary to stress concentration is a concern, any means of decreasing the degree of required compression, or eliminating that compression, is advantageous.

Figure 5:
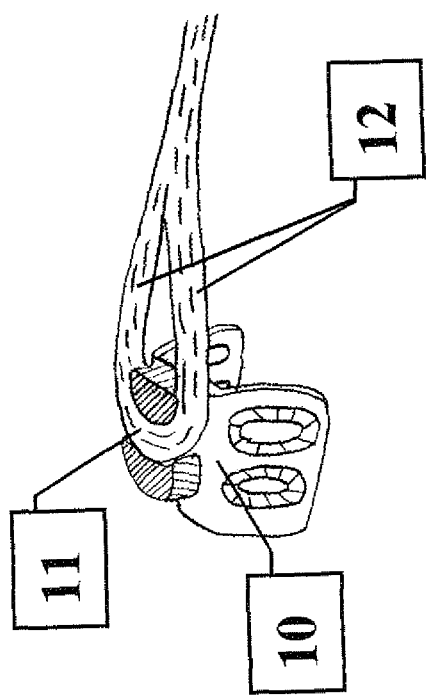
FIG. 5 is a perspective view of a medical device and looped tension member in accordance with an embodiment of the present invention.

FIG. 5 shows an embodiment of the invention in which the knob 1 is machined into a prosthetic anchor block 17 that can be screwed or otherwise attached to directly to a bone to provide a means to attach looped tension member 6 (e.g., an artificial tendon) to the bone. The knob 1 is fashioned by machining channel 2 near the surface of block 17. In this implementation, the anchor block 8 is saddle-shaped such as would be required for securing a prosthetic patellar, or quadriceps-plus-patellar, tendon to a tibial tubercle. It should be understood that the prosthetic anchor block can assume just about any shape that allows it to be securely attached to the target bone.

Figures 8A, 8B:
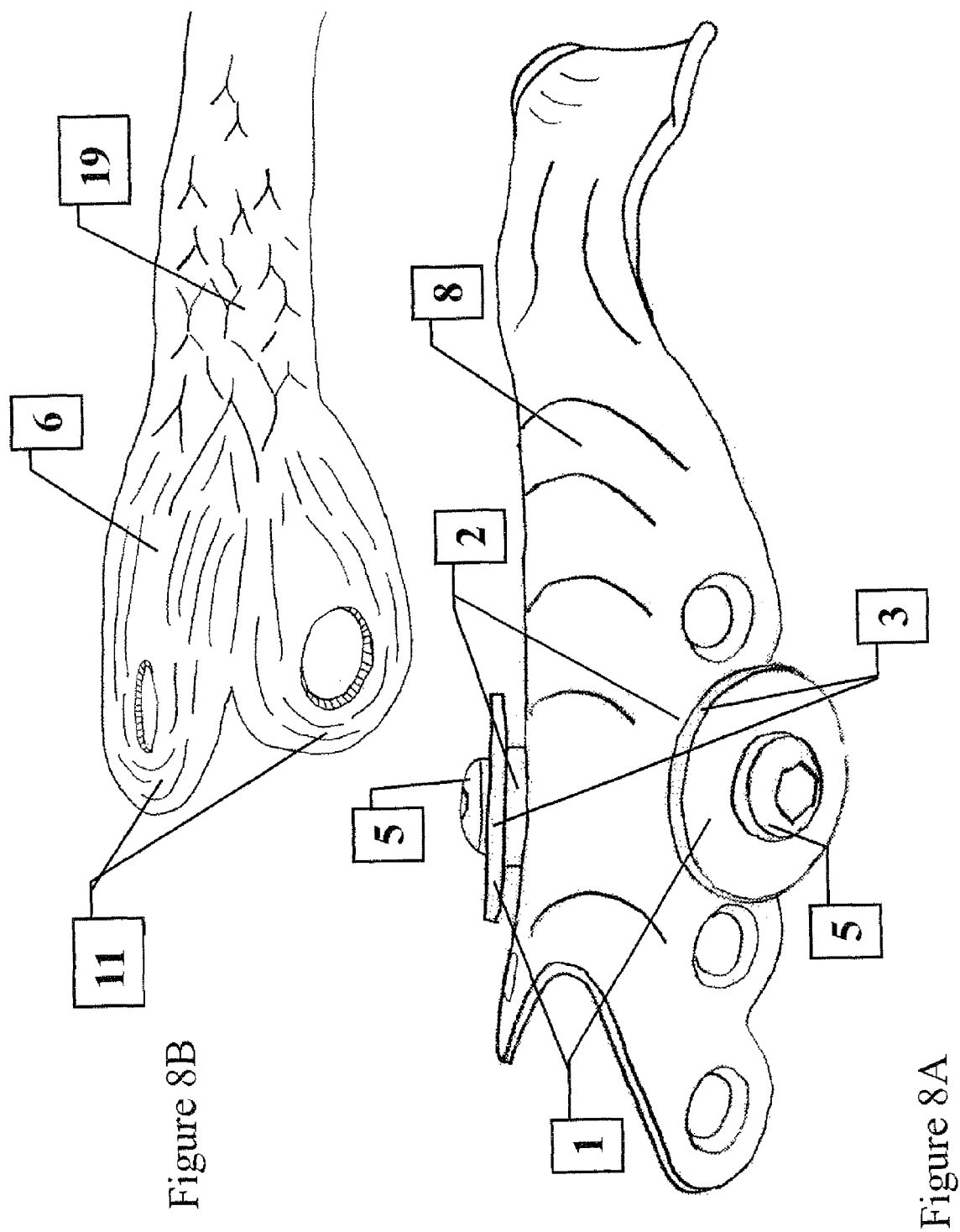
FIG. 8A is a perspective view of a medical device in accordance with another embodiment of the present invention on a bone plate.
FIG. 8B is a perspective view of another embodiment of a looped tension member which fits the bone plate of FIG. 8A.

An alternative embodiment is shown in FIG. 8A wherein anchor block 17 defines bone plate 8 which includes two knobs 1. One advantage of the embodiment of FIG. 8A is that the forces may be distributed across the bone at the two knobs 1. This embodiment is also advantageous for placement of a tension element on a bone having little tissue coverage, such as attachment of the patella tendon to the tibia. Other embodiments include flat plates and simpler knobs required for attachment of tendon prostheses to a flat region of bone. As will be understood by one familiar with the discipline of orthopaedic reconstruction, straightforward variations of these approaches are means of attachment to prosthetic (titanium alloy, for example) bones, such as required for oncologic reconstruction or extensive revision arthroplasty. In those (prosthetic bone) applications, the knob 1 may be integrally machined, integrally cast/molded, or formed separately and fixed by screw, rivet, or other means.

With reference to FIG. 11, as indicated above, another aspect of the invention is the operational coupling of a tissue with energy converter 18 via anchor block 17 having knob 1 and looped tension member 6. The anchor block 17 with knob 1 is coupled to the energy converter 18 providing an attachment locus for the looped tension member 6. The looped tension member 6 is coupled to the knob 1 and to tissue, such as a muscle, thereby enabling the coupled muscle to drive the energy converter 18. Energy converters convert one form of energy into another form. For example, an energy converter may convert linear mechanical energy from a contracting muscle into electrical energy or rotational mechanical energy. Examples of energy converters are taught by U.S. Pat. Nos. 5,718,248 and 5,888,186, (both of the aforementioned patents are incorporated by reference herein). In this example, the knob 1 portion is cast or machined on, or mechanically fixed to, actuator arm 16 of energy converter 18.

Figure 12:
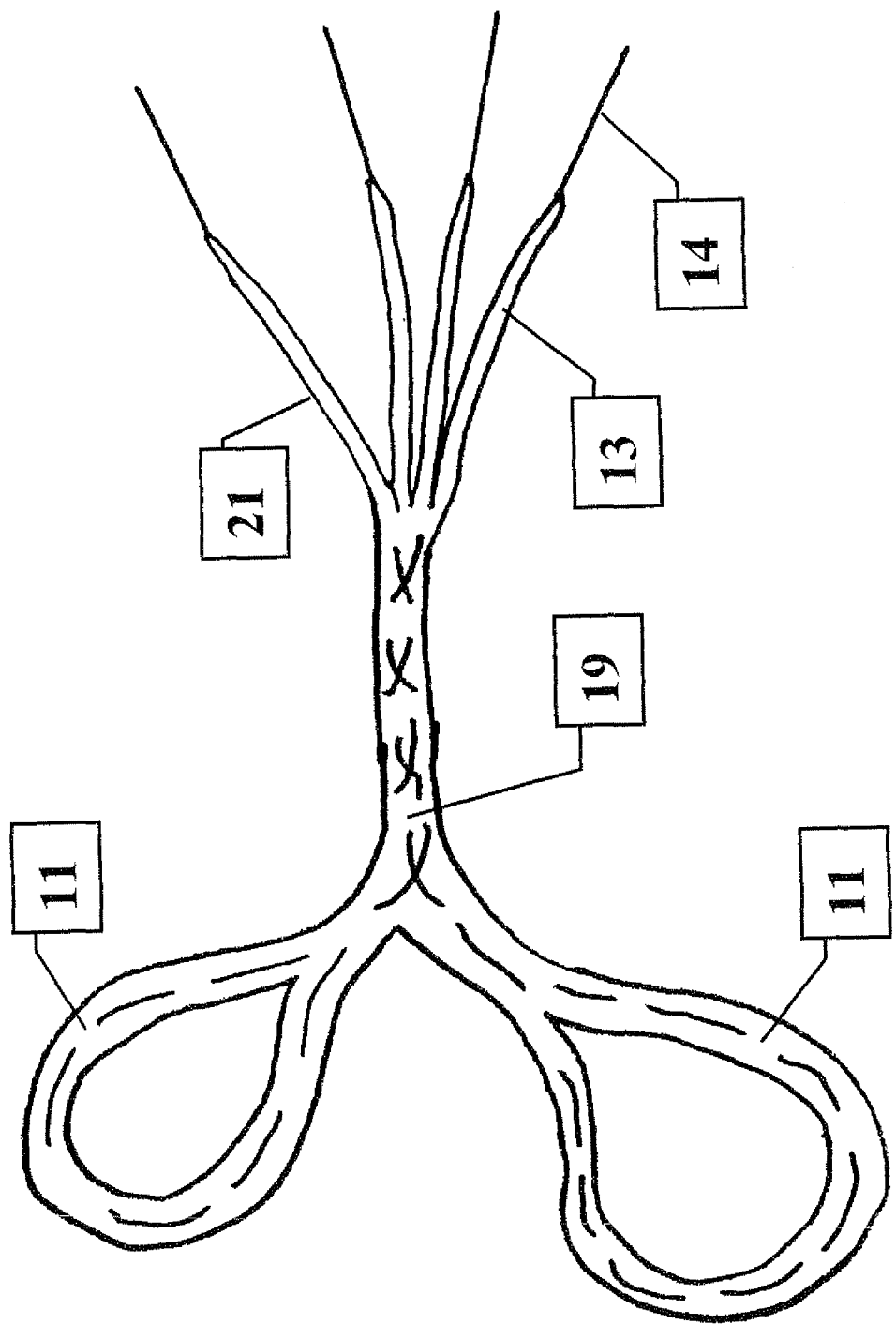
FIG. 12 is a side elevational view of another embodiment of a looped tension member.

As mentioned above and best shown in FIGS. 5-7, 8B and 12, the looped tension member 6 includes a loop portion 11 having two 'arms' 12 and a tissue engaging portion 21. The loop portion is configured to engage the knob 1. The tissue engaging portion 21 is configured for engaging a tissue of the subject, such as a muscle. Connecting the loop portion 11 and the tissue engaging portion 21 there may be an intermediate portion 19 (FIG. 12). In one embodiment, as shown in FIGS. 8B and 12, the looped tension member 6 includes two loop portions 11 extending from a single intermediate portion 19. A looped tension member 6 having more than two loop portions 11 is contemplated.

The looped tension member 6 is comprised of biocompatible fibers, filaments, wires, or other components. The fibers, filaments or wires may include polymer fiber, metal wire, or glass filament as nonlimiting examples or any other material with appropriate tensile properties. The fibers proceed from one end of the loop to the other with no discontinuity for a durable connection with the tissue, thus the fibers of the looped tension member 6 define a continuous unit. The fibers may be formed into bundles or tows 13. The fibers of the intermediate portion 19 and or the loop portion 11 may be braided. Similarly, the intermediate portion 19 and or the loop portion 11 may be at least partially encased in a sheath. The sheath may be a polymer covering, a fabric, wrapped fibers, or any suitable material.

Figure 6:
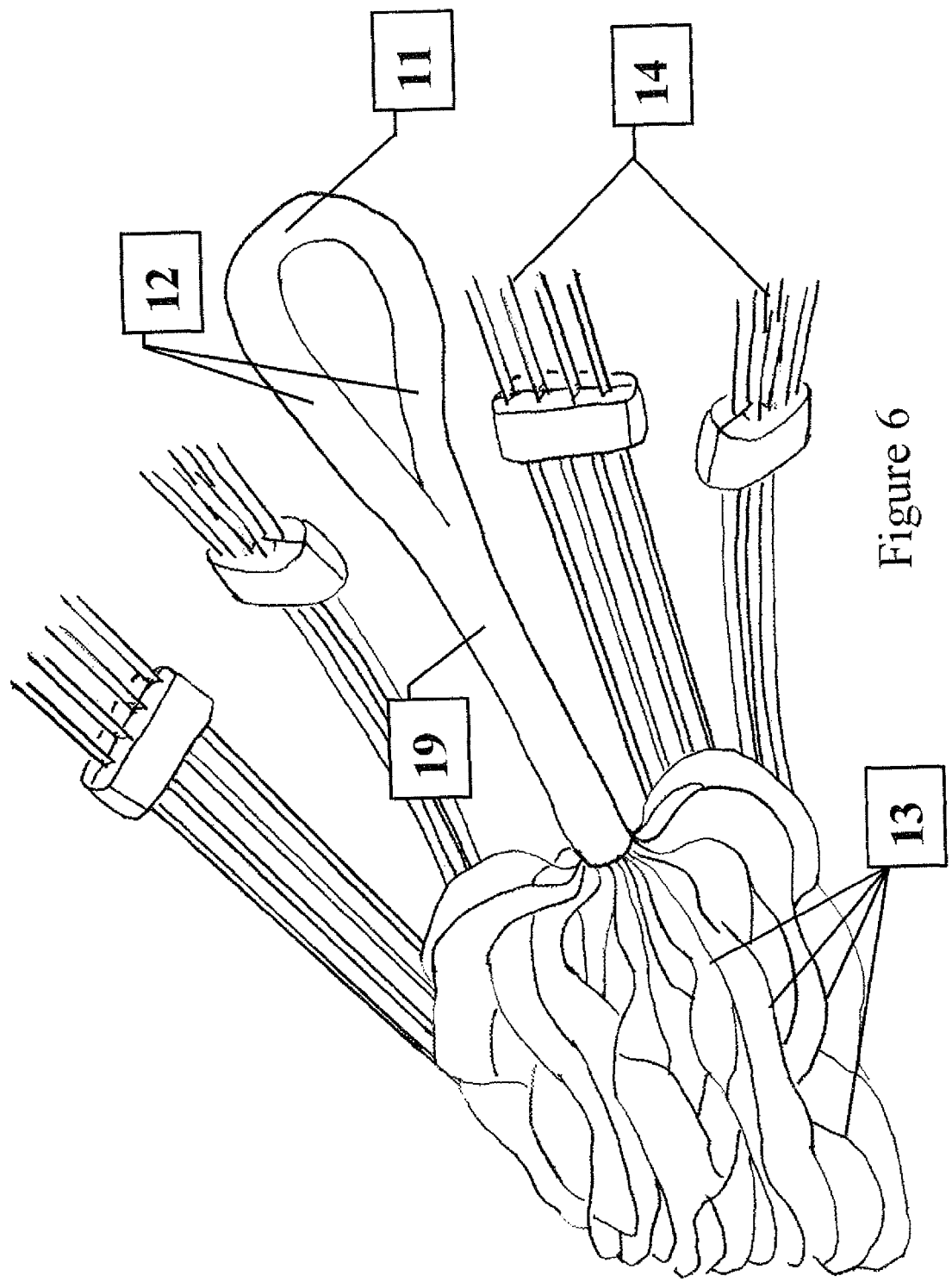
FIG. 6 is a perspective view of another embodiment of a looped tension member.

The "loop" component 11 of the looped tension member 6 is an improvement upon a muscle coupler, such as disclosed in U.S. Pat. Nos. 6,214,047 and 6,733,510, and, thus, may be placed, or utilized, by the methods taught in those patents (both of the aforementioned patents are incorporated by reference herein). In brief, each of the arms 12 extending from the loop portion 11 comprise fibers that subsequently divide into one or more bundles 13 or tows of fibers, each of which is equipped with an insertion portion, e.g., a needle 14 (FIG. 7), configured to be inserted into the tissue of the subject (FIG. 6). Exemplary tissues include muscle tissue, connective tissue, and bone.

Figure 2:
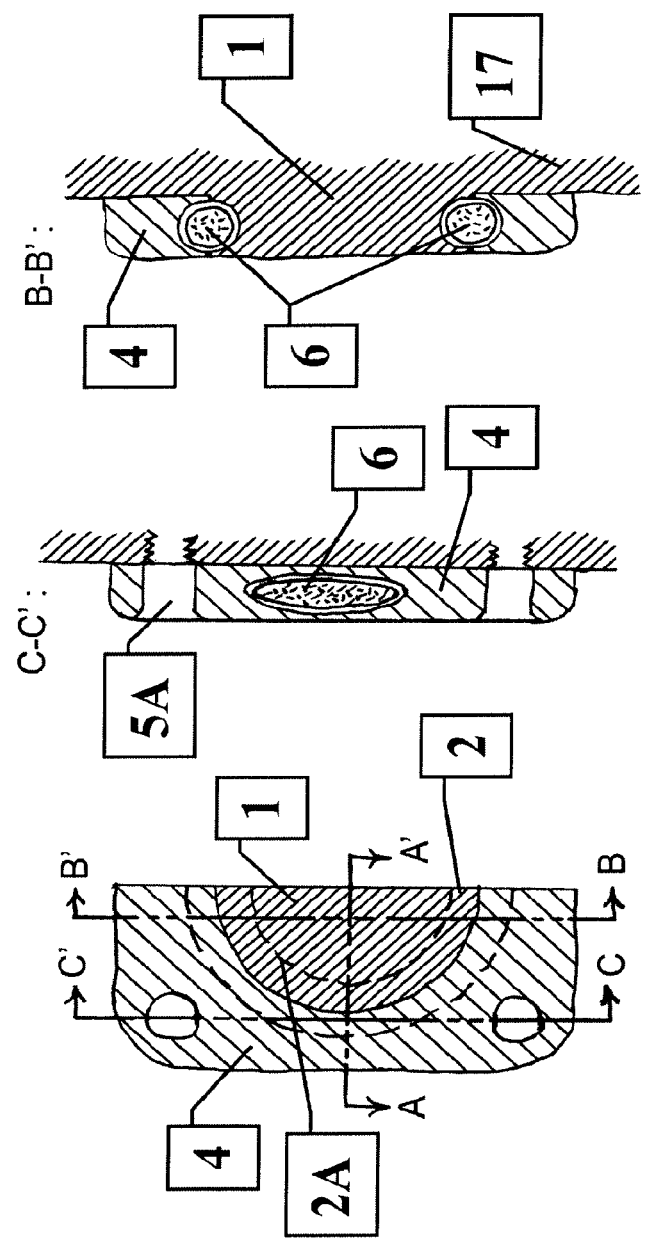
FIG. 2 is a set of cross-sectional views of FIG. 1.
Figure 2:
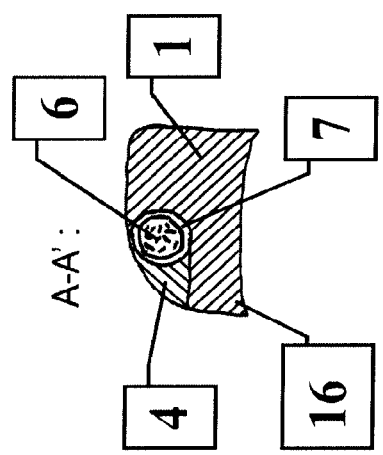
Figure 3:
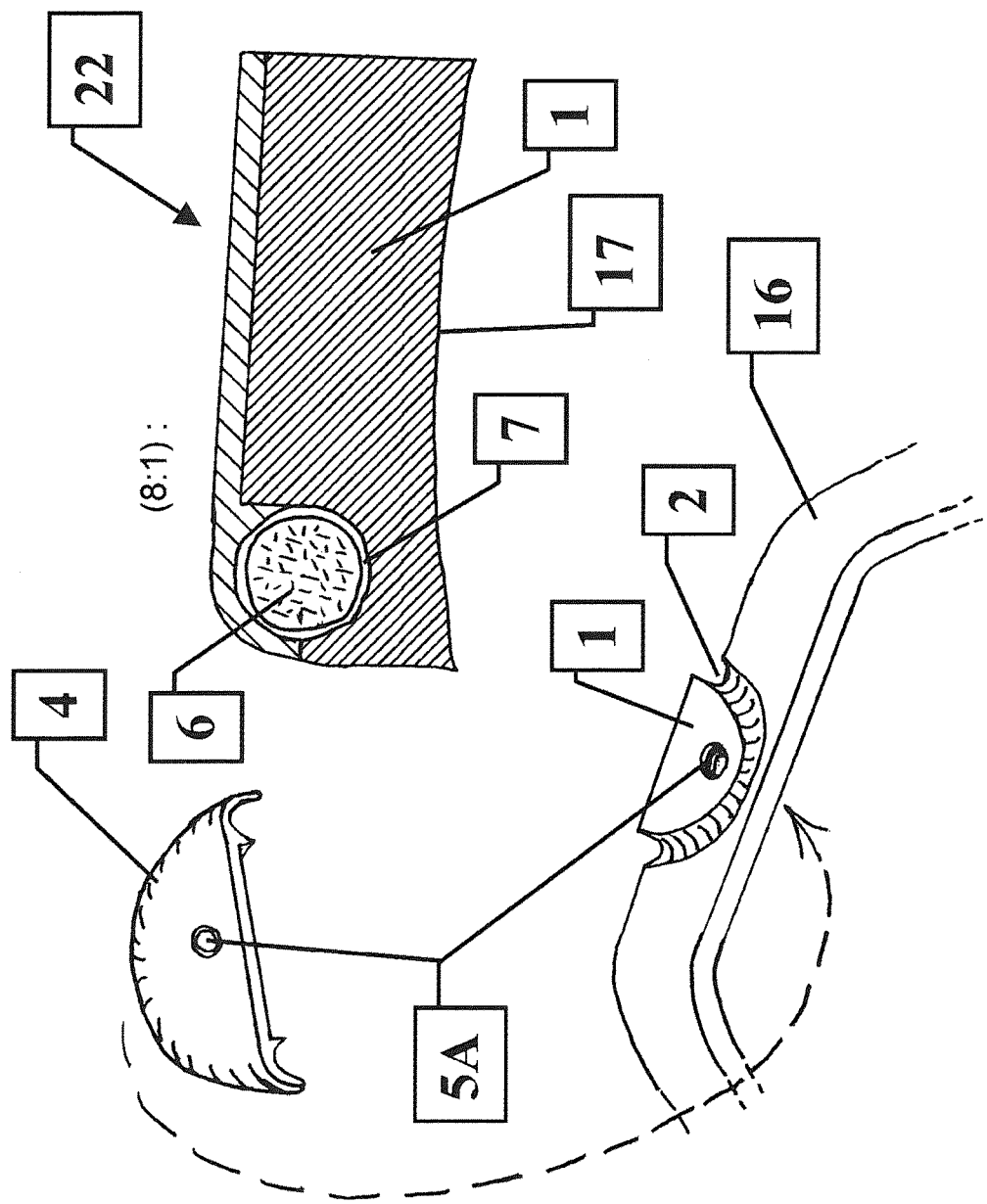
FIG. 3 is a perspective view and a cross-sectional view of a medical device in accordance with another embodiment of the present invention.
Figure 7:
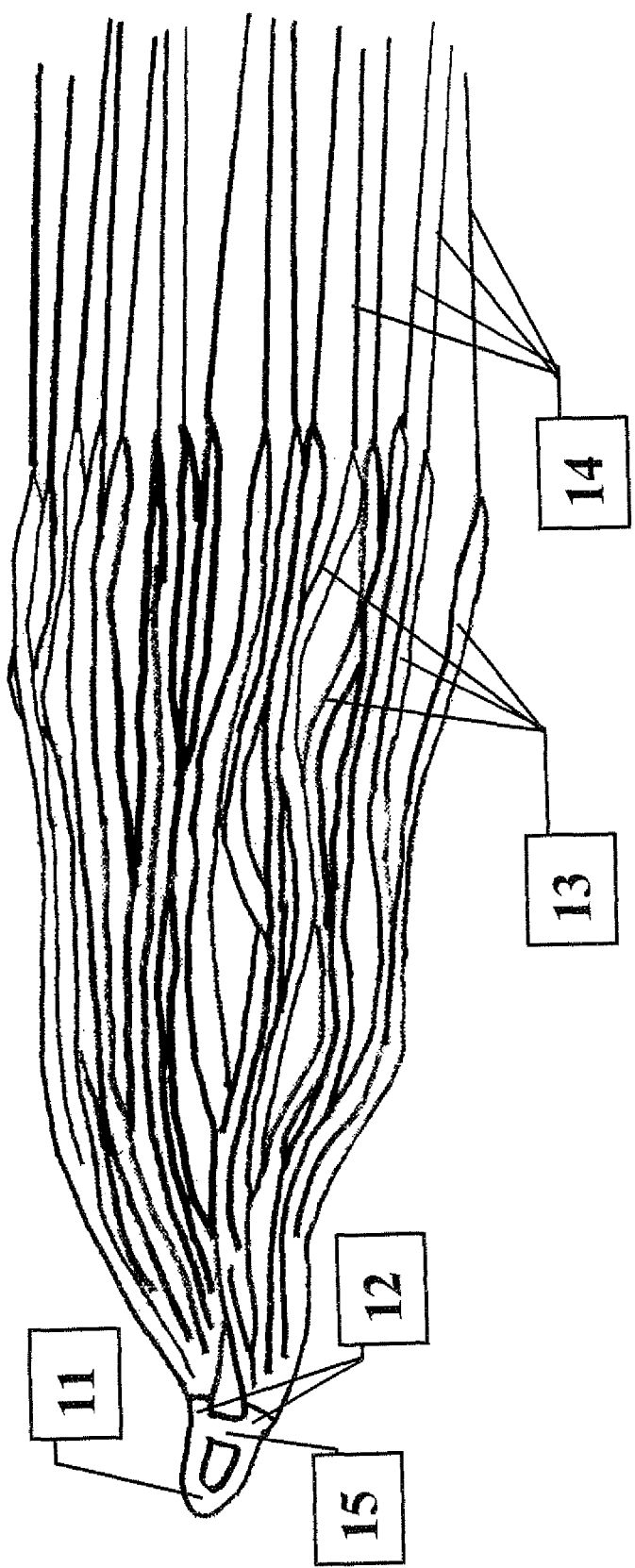
FIG. 7 is a perspective view of another embodiment of a looped tension member.

Fixation of the loop portion 11 of the looped tension element 6 to knob 1 is achieved by placing the loop portion 11 about the knob. The security of placement may be augmented by (a) securing a cap 4, nonlimiting examples of which are shown in FIGS. 1, 2, and 3, (b) completing the encirclement of the knob 1 by a band 15, such as an elastic band composed of a knitted fabric impregnated by an elastomeric polymer of which a nonlimiting example is shown in FIG. 7, or, (c) both.

Concerning the "knob" component, the knob 1 can be integral with, or attached to, and a potential improvement upon, the part or device (bone plate, prosthetic bone, energy converter or other) that is to be driven or moved by forces applied to the loop by the tissue's action, i.e., muscle contraction.

It will be appreciated that specifications and tolerances for the individual parts will determine whether looped tension member 6 does or does not move during operation between cap 4 and channel 2. Generally, these specifications will be such that motion does not occur during normal circumstances after attachment and fixation of cap 4. The only potential disrupting force for the mechanical stability is the net difference in the tension between the two arms 12 of the loop portion 11 as they come together at the intermediate portion 19, which is less (and generally either much less) than the force transmitted from the looped tension member 6 to the knob 1. It will also be appreciated that the required resistance to sliding, and thus the compressive force required, between cap 4 and channel 2, if required at all, will be substantially less than that required between bone or bone plate 8 and compression plate 9 of prior practice. Thus, the stress concentration induced by that compression in looped tension member 6 will be accordingly less, if not negligible.

It is important also to reduce stress concentration resulting from bending of the loop portion 11 of the looped tension member 6 at the entrance or exit from channel 2. This may be achieved by flared or trumpet-shaped ends 20 for channel 2, as shown in FIGS. 9B, 10, and 11, and by further encasing tensile member 6 in an elastomeric sheath 7, as shown in FIG. 2. It will be further appreciated that elastic sheath 7 may aid in spatially distributing, and thus lessening maximum levels of, compressive stress induced by the tightening of cap 4 and channel 2 around looped tensile member 6.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed:

1. A surgical implant for affixing a prosthetic tension member within a patient, comprising:
    an anchor block having a first surface, the anchor block configured to be secured within the patient;
    at least one knob including a channel and a rim, the knob rigidly extending from the first surface of the anchor block to the rim and through the channel, a first plane, and a second plane, the first plane being offset from the first surface between the first surface and the rim, and the second plane being transverse to the first plane; and
    the channel circumscribing at least a portion of the knob in the first plane between the first surface and the rim, the channel having a curved surface in the first plane and an arcuate profile in the second plane for receiving a looped tension member therein,
    wherein the anchor block and the knob are each formed from a biocompatible material and further wherein the anchor block defines an actuator arm, the actuator arm being coupled to an energy converter configured to convert linear mechanical energy to at least one of an electric energy, a rotational mechanical energy, a pneumatic energy, and a hydraulic energy.

2. The surgical implant of claim 1 further including a cap disposed about at least a portion of the knob, the cap configured to assist in keeping the looped tension member in place.

3. The surgical implant of claim 1 wherein the at least one knob includes two or more knobs, each configured to engage a looped tension member.

4. The surgical implant of claim 1 wherein the arcuate profile is continuous through the channel.

5. The surgical implant of claim 1 wherein the curved surface of the channel circumscribes the knob between 90 degrees and 270 degrees in the first plane.

6. The surgical implant of claim 2 wherein the cap is positioned adjacent to the knob to further define the arcuate profile of the channel, the arcuate profile at least partially enclosed for securing the looped tension member therebetween.

7. The surgical implant of claim 6 wherein the arcuate profile is fully enclosed for securing the looped tension member therebetween.

8. The surgical implant of claim 1 wherein the curved surface is convex in the first plane and the arcuate profile is concave in the second plane.

9. A prosthetic tendon system for surgical implantation within a patient, comprising:
    at least one looped tension member, the at least one looped tension member having a looped portion and a tissue engaging portion, the tissue engaging portion configured to engage a tissue in the patient; and
    a surgical implant including:
        an anchor block having a first surface, the anchor block configured to be secured within the patient;
        at least one knob including a channel and a rim, the knob rigidly extending from the first surface of the anchor block to the rim and through the channel, a first plane, and a second plane, the first plane offset from the first surface and between the first surface and the rim, and the second plane being transverse to the first plane; and
        the channel circumscribing at least a portion of the knob in the first plane between the first surface and the rim, the channel having a curved surface in the first plane and an arcuate profile in the second plane,
    wherein the looped portion of the at least one looped tension member is oriented about the knob and within the channel and the anchor block and the knob are each formed from a biocompatible material and,
    further wherein the at least one looped tension member further includes an intermediate portion and a plurality of unbraided bundles of the tissue engaging portion, the at least one looped portion connected to the plurality of bundles by the intermediate portion, and the at least one looped portion, the intermediate portion, and the plurality of bundles defining a continuous unit wherein each of the plurality of unbraided bundles is comprised of a plurality of elongated fibers, each bundle being equipped with a needle, the needle being securely attached to an end of the fibers.

10. The prosthetic tendon system of claim 9 wherein the anchor block defines one of a bone plate, an actuator arm, or prosthetic bone.

11. The prosthetic tendon system of claim 9 wherein the at least one looped portion, intermediate portion, and plurality of unbraided bundles are comprised of elongated fibers, and each of the fibers being continuous through the looped portion, the intermediate portion, and a pair of the bundles.

12. The prosthetic tendon system of claim 11 wherein the fibers are braided in the intermediate portion.

13. The prosthetic tendon system of claim 9 wherein the at least one looped portion includes two looped portions extending from the intermediate portion.

14. The prosthetic tendon system of claim 9 further including an operational device, the surgical implant being integral with the operational device.

15. The prosthetic tendon system of claim 14 wherein the operational device is an energy converter configured to convert mechanical energy to at least one of an electric energy, a pneumatic energy, and a hydraulic energy.

16. The prosthetic tendon system of claim 9 wherein the channel has an internal height, the at least one looped tension member being oriented about the knob following the curved surface within the channel for a distance that is more than double the internal height.

17. A method for implanting a prosthetic tendon system in a patient comprising the steps of:
    positioning a medical device including an anchor block having a first surface and at least one knob including a channel and a rim within the patient, the knob rigidly extending from the first surface to the rim through the channel, a first plane, and a second plane, the first plane offset from the first surface between the first surface and the rim, and the second plane being transverse to the first plane;

placing at least one looped portion of a looped tension member having a tissue engaging portion about the knob;

receiving the at least one looped portion against a curved surface and an arcuate profile of the channel circumscribing at least a portion of the knob in the first plane between the first surface and the rim, the curved surface of the channel being in the first plane and the arcuate profile of the channel being in the second plane; and engaging a tissue in the patient with the tissue engaging portion of the looped tension member wherein the at least one looped portion is placed about the knob prior to engaging the tissue of the patient with the tissue engaging portion.

18. The method of claim 17 further comprising securing a cap about a portion of the knob.

* * * * *